US012303202B2

(12) United States Patent
Yoon

(10) Patent No.: US 12,303,202 B2
(45) Date of Patent: May 20, 2025

(54) METHOD AND APPARATUS FOR LOCATING THE VISUAL AXIS ON THE SURFACE OF THE CORNEA

(71) Applicant: University of Rochester, Rochester, NY (US)

(72) Inventor: Geunyoung Yoon, Houston, TX (US)

(73) Assignee: University of Rochester, Rochester, NY (US)

(*) Notice: Subject to any disclaimer, the term of this patent is extended or adjusted under 35 U.S.C. 154(b) by 734 days.

(21) Appl. No.: 17/594,984

(22) PCT Filed: May 11, 2020

(86) PCT No.: PCT/US2020/032289
§ 371 (c)(1),
(2) Date: Nov. 4, 2021

(87) PCT Pub. No.: WO2020/231894
PCT Pub. Date: Nov. 19, 2020

(65) Prior Publication Data
US 2022/0287562 A1 Sep. 15, 2022

Related U.S. Application Data

(60) Provisional application No. 62/846,890, filed on May 13, 2019.

(51) Int. Cl.
*A61B 3/15* (2006.01)
*A61B 3/113* (2006.01)
*A61B 3/117* (2006.01)

(52) U.S. Cl.
CPC .............. *A61B 3/152* (2013.01); *A61B 3/113* (2013.01); *A61B 3/1173* (2013.01)

(58) Field of Classification Search
CPC ....... A61B 3/152; A61B 3/113; A61B 3/1173; A61B 3/103
(Continued)

(56) References Cited

U.S. PATENT DOCUMENTS 4,875,767 A 10/1989 Wright
2006/0184243 A1* 8/2006 Yilmaz .................. A61F 2/148
623/4.1

(Continued)

FOREIGN PATENT DOCUMENTS

JP H08196511 A 8/1996
WO WO-2006047534 A1 5/2006

OTHER PUBLICATIONS

ISA/European Patent Office International Search Report and Written Opinion dated Jul. 20, 2020 for corresponding International Application No. PCT/US2020/032289 (12 pgs).

*Primary Examiner* — Tuyen Tra
*Assistant Examiner* — Rahman Abdur
(74) *Attorney, Agent, or Firm* — Harris Beach Murtha Cullina PLLC

(57) ABSTRACT

A method to find a visual axis of an eye includes illuminating a light source pinhole by a light including at least two different wavelengths; projecting an image of the light source pinhole through a translatable pinhole and through a pupil of the eye onto a retina of the eye; generating a projected image of the translatable pinhole on an anterior surface of the eye or a contact lens; adjusting a position of the translatable pinhole in a plane about parallel to a plane of a cornea of the eye until two different dots viewed on the retina merge into one dot; and indicating by the projected image of the translatable pinhole a location of where the (Continued)

visual axis of the eye intersects the cornea or the contact lens. An apparatus to measure a visual axis of an eye is also described.

21 Claims, 5 Drawing Sheets

(58) Field of Classification Search
USPC .......................................................... 351/211
See application file for complete search history.

(56) References Cited

U.S. PATENT DOCUMENTS

| | | | |
|---|---|---|---|
| 2011/0069281 A1* | 3/2011 | Redmann | G03B 21/00 |
| | | | 353/121 |
| 2011/0309231 A1* | 12/2011 | Cooper | G02B 21/16 |
| | | | 250/201.2 |
| 2015/0070655 A1* | 3/2015 | Rossi | G02B 21/0076 |
| | | | 351/246 |
| 2018/0092528 A1* | 4/2018 | Takeno | A61B 3/102 |

* cited by examiner

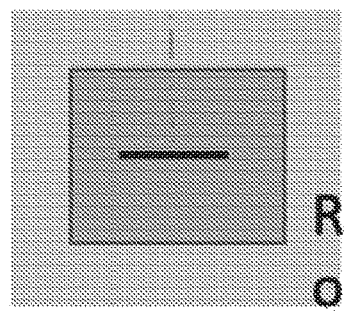
Retina camera for objective method before adjusting the translatable pinhole; two separate spots (red and purple)

After adjusting the translatable pinhole; two separate spots superimposed (white)

METHOD AND APPARATUS FOR LOCATING THE VISUAL AXIS ON THE SURFACE OF THE CORNEA

CROSS-REFERENCE TO RELATED APPLICATIONS

This application is a national stage application under 35 U.S.C. § 371 of PCT Application No. PCT/US2020/032289, filed May 11, 2020, METHOD AND APPARATUS FOR LOCATING THE VISUAL AXIS ON THE SURFACE OF THE CORNEA published as WO/2020/231894A1, which claims priority to and the benefit of U.S. provisional patent application Ser. No. 62/846,890, METHOD AND APPARATUS FOR LOCATING THE VISUAL AXIS ON THE SURFACE OF THE CORNEA, filed May 13, 2019, which application isapplications are incorporated herein by reference in itstheir entirety.

FIELD OF THE APPLICATION

The application relates to an ophthalmic apparatus and method, particularly to an ophthalmic apparatus and method for locating the visual axis of an eye.

BACKGROUND

Advanced methods to improve vision for both young and presbyopic patients have been increasingly popular. They include customized laser refractive surgery, wavefront-guided contact lenses and corneal inlays/onlays. One of the common questions in these methods is where (on conical surface) to apply these methods to achieve optimal outcomes. It is ideal that the correction is applied on the visual axis, however it is very challenging to precisely locate it on the corneal surface in practice because there is no simple way of identifying where the visual axis intersects across the conical surface.

SUMMARY

A method to find a visual axis of an eye includes illuminating a light source pinhole by a light including at least two different wavelengths; projecting an image of the light source pinhole through a translatable pinhole and through a pupil of the eye onto a retina of the eye; generating a projected image of the translatable pinhole on an anterior surface of the eye or a contact lens; adjusting a position of the translatable pinhole in a plane about parallel to a plane of a cornea of the eye until two different dots viewed on the retina merge into one dot; and indicating by the projected image of the translatable pinhole a location of where the visual axis of the eye intersects the cornea or the contact lens.

The step of illuminating can include illuminating the light source pinhole by a first light source of a first wavelength and a second light source of a second wavelength. The step of illuminating can include illuminating the light source pinhole by a first LED with a red interference filter or a first narrowband red LED, and a second LED with a blue interference filter, or a second narrowband blue LED. A light of the first light source and a light of the second light source can be combined by a beam splitter.

The step of projecting can include projecting an image of the translatable pinhole with a manual x-y position adjustment adjustable in the step of adjusting by a patient in a subjective measurement mode. The step of projecting can include projecting an image of the translatable pinhole with a motorized x-y position adjustment adjustable in the step of adjusting by a processor-based process in an automatic objective measurement mode.

The step of adjusting can include viewing one or two dots with a retina camera.

The step of indicating can include viewing the projected image of the translatable pinhole on the cornea with a pupil camera.

An apparatus to measure a visual axis of an eye includes a light source pinhole illuminated by a first light source having at least first wavelength of light and a second light source having a second wavelength of light different from the first wavelength of light. The light source pinhole is disposed on a main optical axis. An optical assembly is about aligned with the main optical axis. A translatable pinhole is disposed between the optical assembly and the light source pinhole. The translatable pinhole is adjustable in a plane about perpendicular to the main optical axis.

The first light source and the second light source each can include a LED and an interference filter. The first light source and the second light source each can include a laser. The first light source can include about a red light, and the second light source can include about a blue light. The first light source and the second light source can be combined by a beamsplitter.

A lens can be disposed on the main optical axis between the light source pinhole and the translatable pinhole.

The optical assembly can include a lens or a 4f lens system.

The optical assembly can further include a Badal optometer or a trombone system.

The apparatus can include a pupil camera beam splitter disposed in the main optical axis between the translatable pinhole and the optical assembly, and a pupil camera disposed in a pupil camera viewing axis about perpendicular to the main optical axis and in view of said pupil camera beam splitter.

The apparatus can further include a retina camera beam splitter disposed in the main optical axis between the light source pinhole and the translatable pinhole and a retina camera disposed in a retina camera viewing axis about perpendicular to the main optical axis and in view of said retina camera beam splitter.

The translatable pinhole can include a two-axis motorized translatable pinhole.

The apparatus can further include a processor operatively coupled to the two-axis motorized translatable pinhole and a retina camera, the processor programmed to run a visual axis location process. The visual axis location process can automatically move the translatable pinhole to find a position of the translatable pinhole where there is substantially no transverse chromatic aberration of a single dot image of the light source pinhole on a retina of the eye thus indicating the visual axis of the eye by an image of the translatable pinhole projected onto a cornea of the eye or a contact lens where the visual axis intersects the cornea or the contact lens.

The foregoing and other aspects, features, and advantages of the application will become more apparent from the following description and from the claims.

BRIEF DESCRIPTION OF THE DRAWINGS

The features of the application can be better understood with reference to the drawings described below, and the claims. The drawings are not necessarily to scale, emphasis

DETAILED DESCRIPTION

Definitions

Figure 1A:
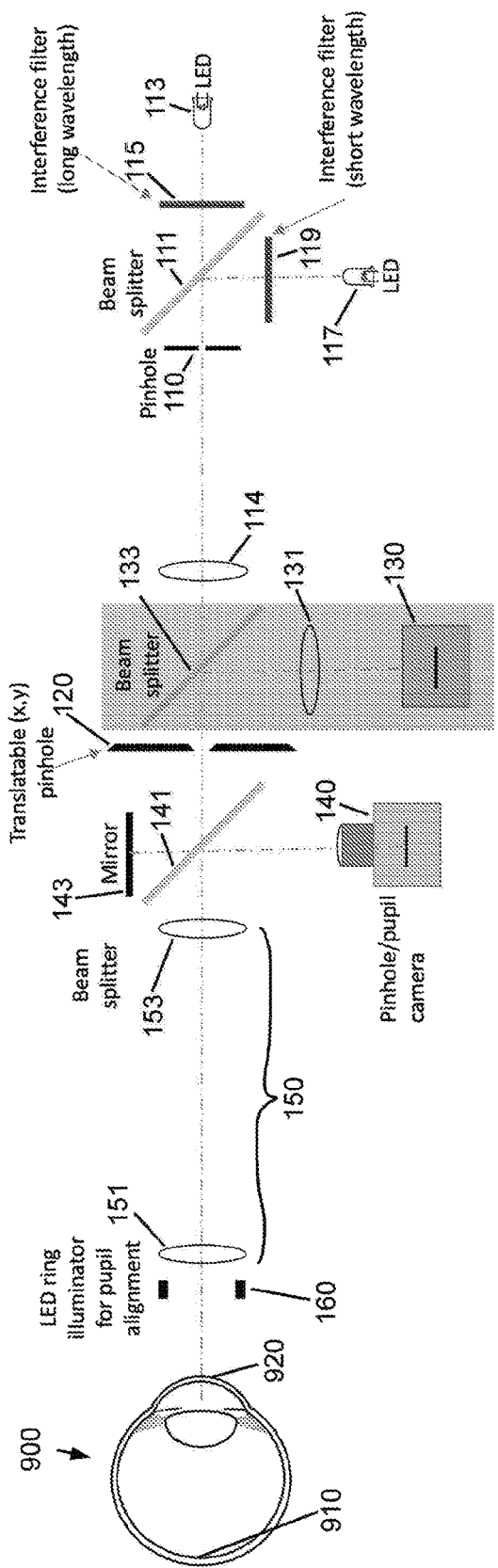
FIG. 1A shows a schematic diagram of an exemplary apparatus according to the Application.

Visual Axis—Light passing into the eye along the visual axis of the eye undergoes substantially no transverse chromatic aberration.

Translatable pinhole position—The position of the translatable pinhole is typically measured with respect to the eye's pupil center or the first Purkinje image as the corneal surface is substantially not visible.

Pupil center and the first Purkinje image—The pupil center and the first Purkinje image are independent reference features that are part of the image from the pupil camera. The pupil center is defined by the center of pupil edge and the first Purkinje image can be defined by the center of the LED pattern (circular array) illuminating the pupil. Either one can be used to determine where the visual axis crosses the corneal surface.

As described hereinabove, advanced methods to improve vision for both young and presbyopic patients have been increasingly popular. They include customized laser refractive surgery, wavefront-guided contact lenses and corneal inlays/onlays. One of the common questions in these methods is where (on corneal surface) to apply these methods to achieve optimal outcomes. It is ideal that the correction is applied on the visual axis, however it is very challenging to precisely locate it on the corneal surface in practice because there is no simple way of identifying where the visual axis intersects across the corneal surface.

Due to this limitation, either the center of the entrance pupil or the coaxially sighted corneal reflex (the first Purkinje image) has been used as the reference axis to align the correction. Any deviations from the true visual axis can cause reduced benefit of the correction and adverse visual symptoms such as halos and glares.

The new method and apparatus described by the Application addresses this critical clinical barrier. The idea is based on the theoretical definition of the visual axis that there should be no transverse chromatic aberration along the true visual axis. A new optical system is described which is capable of locating the point on the corneal surface at which the visual axis crosses it. The new apparatus and method can be performed both subjectively (by relying on patient's adjustment) or objectively (by using a retina camera). The apparatus can be developed as a standalone clinical device and used for any vision correction methods applied on and near the corneal surface.

The principle of operation is based on there being substantially no transverse chromatic aberration along the true visual axis. Light entering the eye off the visual axis is subject to a refraction which varies with wavelength caused by a non-zero transverse chromatic aberration. Off of the visual axis, the light of a first wavelength undergoes a first refraction traveling through the parts of the eye to the retina, and the light of the second wavelength of light undergoes a second refraction, different from the first refraction. When the light enters the eye off the visual axis, a light source having at least two different wavelengths of light will appear in at least two different locations on the retina as two dots.

However, if the same multispectral light (e.g. having two-wavelengths of light) enters the eye substantially on the visual axis, there is substantially no transverse chromatic aberration, and there will be only one common spot of illumination on the retina. Moreover, the combination of the two wavelengths will result in a third color. For example, when a blue light and a red light is combined, on the visual axis there will appear an about white light.

In the new apparatus, a light which includes two different wavelengths illuminates a light source (LS) pin hole. The light with two different wavelengths can be provided, for example, by two separate light sources where the light from the first light source of the first wavelength is combined with the light from the second light source at the second wavelength by a beam splitter. By optics described in more detail hereinbelow, which includes a front-end lens system closest to the eye, an image of the LS pin hole near the light sources (typically LEDs) is formed in the retinal plane of the eye.

Disposed between the front-end lens system and the LS pin hole is a translatable pinhole. The translatable pinhole can be moved in both of an x and a y direction in a plane about perpendicular to the visual axis. An image of the translatable pinhole is formed on the corneal plane of the eye.

The pinhole near the light sources (e.g. LEDs) forms an image on the retina plane which guides a subject or the retina camera (e.g. a fundus camera) to minimize transverse chromatic aberration by moving the translatable pinhole. The subject (subjective mode) or fundus camera (objective mode) sees the image of the LS pinhole near the LEDs.

A pupil camera views the image of the translatable pinhole on the cornea plane and provides the crossing point between the visual axis and the conical surface.

As described in more detail hereinbelow, the apparatus is first aligned with the eye by fixation on a target (the image of the LS pin hole). Typically, the patient places their head into any suitable ophthalmic patient mount, such as, for example, an adjustable chin rest system. The ophthalmic patient mount typically includes 3-axis adjustment, x, y, and z. Such ophthalmic patient mounts are well known to those skilled in art of ophthalmic instrumentation and apparatus.

The x-y axis of the ophthalmic patient mount place the patient's eye in front of the new apparatus where the images in the two planes, the retinal plane and the corneal plane can be made in focus by the z axis adjustment, and now according a first step of the new method, the eye can be situated in front of the apparatus where at first order, with the translatable pin hole at about x=0, and y=0, the translatable pinhole is roughly centered in the pupil of the eye, such as by use of a pupil camera.

Where the patient needs further corrective action to provide an in-focus image of the light source pinhole on the retina of the patient's eye, there can be additional corrective optics along the main optical axis of the apparatus. For example, the apparatus can include in the main optical path a Badal optometer (or trombone system). This addition correction when used changes the distance between the two lenses for the 4-f system to induce different optical power by moving a right-angle prism (or two mirrors instead) that corrects for the eye's refractive error without changing imaging magnification.

Once the ophthalmic patient mount is initially adjusted, and the patient can see a substantially in focus image of the LS pin hole, x-y movement of the translatable pin hole moves the image of the translatable pin hole in lateral x-y directions across the corneal plane. As discussed hereinabove, light entering the pupil of the eye off the visual axis will experience a non-zero transverse chromatic aberration causing two different spots to appear at two different locations on the retina of the patient's eye. However, when the x-y position of the translatable pin hole is adjusted (such as by a manual or motor driven x-y vernier control) so that the light enters the eye at substantially the visual axis, there is now substantially no transverse chromatic aberration and there is only one spot of light on the retina, and the image of the transverse pinhole on the cornea is then substantially at the visual axis.

In a subjective mode, once the ophthalmic patient mount is initially adjusted, the patient themselves can adjust the x and y controls of the translatable pin hole until they see just one dot. Persons with good color vision will see two different dots of two different colors merge into one dot of an about white color. Persons with lesser color vision (e.g. color blind) will see to dots of possibly similar or same color merge into one dot. Note that is unimportant that the patient perceives the two colors. However, there must be at least two colors (at least a first and a second wavelength) because it is the difference of refraction of different wavelengths of light off visual axis that causes the two spots which merge into one spot when the light enters the eye at the visual axis.

Similarly, in an objective mode, two spots of light are merged into one, however the difference is that a retinal camera views the spots on the retina of the eye, and a processor drives a control process that operates both of an x and a y motor controlling the position of the translatable pinhole until the automatic (objective) process merges the two spots to one spot. At the point of a single spot registered on the retinal camera, the pupil camera can record the visual axis of the eye by recording the location of the image of the translatable pinhole on the corneal plane. In the automatic objective mode, it is similarly unimportant if the retina camera can register each of the two colors. However, a detection or registration of the two colors can also be used by the automatic process to enhance location of each of the spots and/or the process of moving the translatable pinhole to cause a merging of the two dots (e.g. a red dot and a blue dot) into one dot (e.g. about white) at the visual axis. For example, a color sensitive registration of the merged dot can be used to indicate a successful location of the visual axis and to terminate the automatic process of adjusting or stepping the x and/or y motor adjustment of the translatable pinhole.

It can now be better appreciated in analogous feedback and control terms, that the sensed or "feedback" parameter is the sensed distance between the two spots on the retina of the eye. The control loop "plant" includes the motor-controlled position of the translatable pin hole. During a measurement to find the actual visual axis, the "error" of the distance between the two spots is automatically brought to substantially zero, where the two dots overlap into one dot. In the subjective mode, the patient can manually adjust the x-y position of the translatable pinhole to merge the dots into one. In the objective mode, a processor based control loop drives at least one or more actuators (typically two motors, such as stepper motors, one for x, one for y translation) until the distance between the centers of the dots is substantially zero, as measured by a retina camera, such as, for example, a Fundus camera.

While, the merging of two separated spots (distance between the spots on the retina of the eye) into one spot (substantially zero distance between the spots) is how the visual axis can be identified, more sophisticated systems can also make use of the two colors of the dots, which merges into one dot of a third color. For example, typically a red dot and a blue dot merge into an about single white dot.

FIG. 1A shows a schematic diagram of an exemplary apparatus according to the Application. A light having two wavelengths is provided at the LS pinhole 110 by a first LED 113 and a first red interference filter 115 (long wavelength), and a second LED 117 and a second blue interference filter 119 (short wavelength). The red light and the blue light are combined by beam splitter 111. Lens 114 combined with the front-end lens system 150 closest to the eye forms an in-focus image of the LS pin hole in the retinal plane 910 of the eye 900. Note that a narrowband red LED and a narrowband blue LED can be used without an interference filter, as an alternative to separate broadband LEDs and interference filters.

Translatable pinhole 120 is disposed between the LS pinhole 110 and a front-end optical assembly 150. Translatable pinhole 120 can be manually adjustable in the x and y directions by manual vernier controls for a manual x-y adjustment and/or controlled by motors, such as, for example, stepper motors for operation in an objective mode by a processor based automatic control.

The front-end optical assembly 150 includes at least one or more lenses to provide an in-focus image of the translatable pinhole 120 on the surface of the cornea 920 of the eye 900. In the exemplary apparatus of FIG. 1A, the front-end optical assembly 150 includes a 4f lens two lens system where the distance from the lens 151 closes to the eye 900 is f, and the distance between the two lenses 151, 153, is 2f.

In an objective mode for automatic control and measurement of the visual axis of eye 900, a retina camera 130, such as, for example, a Fundus camera, observes the image of the LS pinhole 110 on the retina 910 of eye 900. A beam splitter 133 provides a view of the image of the retina 910 to the retina camera 130 via focusing lens 131. It is unimportant whether focusing lens 131 is a separate lens, or a part of the retina camera. The primary purpose of the retina camera, when present, is to observe the distance between the two spots on the surface of the retina, and optionally the color of the two spots, and a third color when the two spots overlap to create one spot of a third color, typically an about white color. The optional retina camera 130 can supplement or replace a direct visual observation by the patient.

The pupil camera 140 observes an in-focus image on the surface of the cornea 920 via beam splitter 141 and mirror 143. The pupil camera 140 first aids in the initial alignment of the x-y-z positioning of the ophthalmic patient mount. Then after the two spots of the LS pinhole image are merged into one spot on the retina, the pupil camera 140 provides an image of translatable pinhole on the surface of the cornea 920 where the visual axis intersects the plane of the cornea, the desired measurement of the new apparatus.

Another light source 160, typically a white light, is provided about in front of or about on a front surface of the front-end optical assembly 150. The purpose of light source 160, an LED ring illuminator in FIG. 1A, is to light the anterior surface of the eye 900 to provide illumination for the pupil camera 140.

Figure 1C:
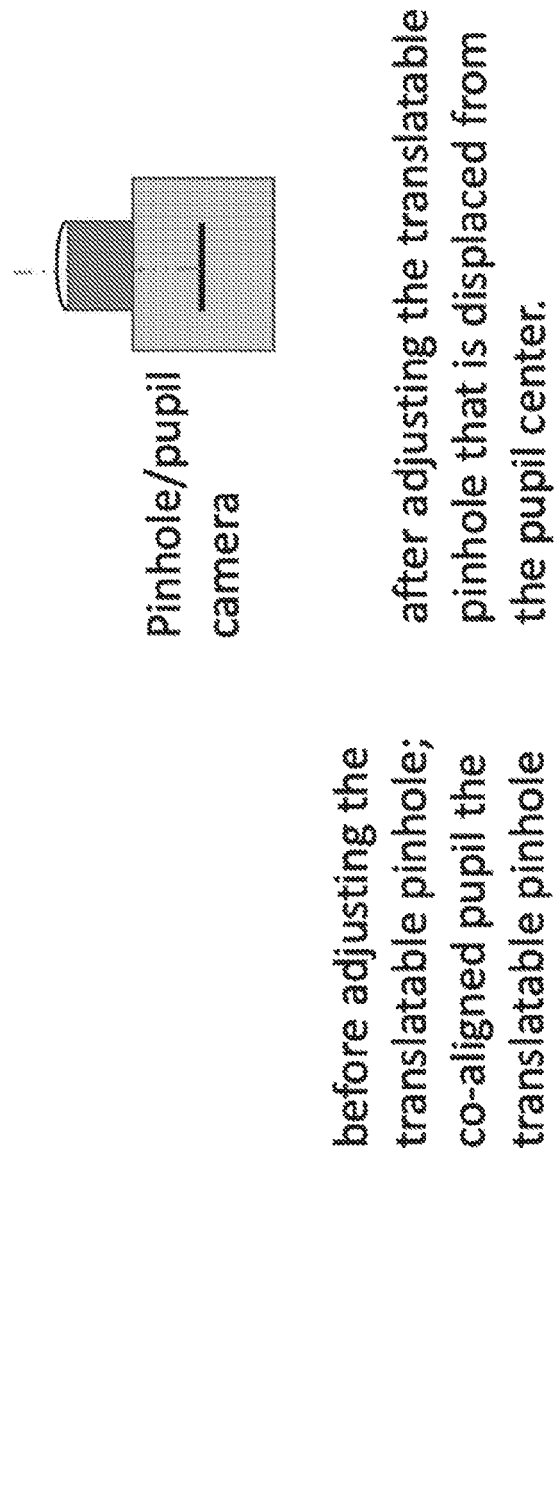
FIG. 1C is an exemplary image of the surface of the cornea after adjustment of the translatable pinhole.
Figure 1C:
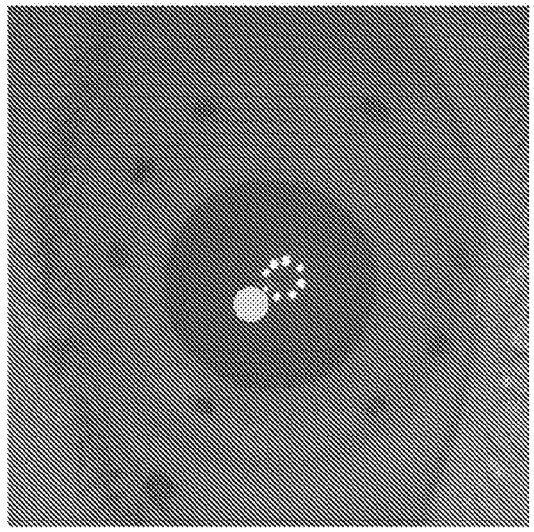
Figure 1B:
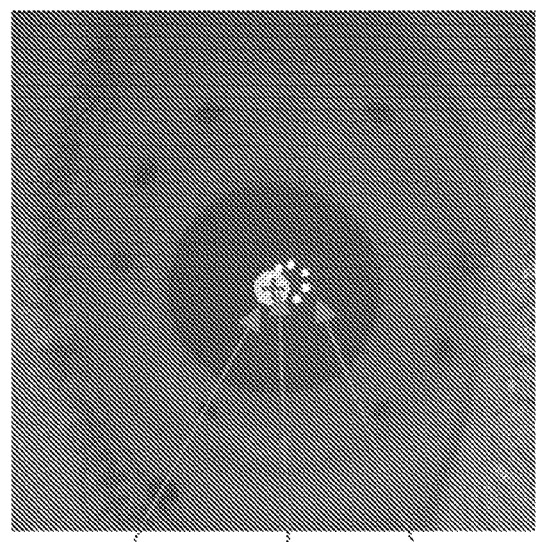
FIG. 1B is an exemplary image of the surface of the cornea before adjustment of the translatable pinhole.

Exemplary conceptual images—FIG. 1B is an exemplary image of the surface of the cornea 920 after adjustment of the ophthalmic patient mount (not shown in FIG. 1A), and before adjustment of the translatable pinhole. The ophthalmic patient mount is first adjusted so that the image of the of the translatable pinhole 120 on the surface of the cornea 920 is in-focus (z), and the image of the translatable pinhole 120 is about in the center of the pupil at about the physical center of the pupil of the patient. This first adjustment of the ophthalmic patient mount in x, y, and z is made while the patient looks at the LS pinhole 110 image as a fixation target.

FIG. 1C is an exemplary image of the surface of the cornea 920 after adjustment of the translatable pinhole 120 so that both color dots are merged into one dot as an indication of substantially no transverse chromatic aberration along the now measured true visual axis. In the exemplary image of FIG. 1C, it can be seen that the actual visual axis can, and usually does, differ from the physical center of the pupil. While the deviation of the visual axis from the physical center of the pupil is exaggerated in FIG. 1C to illustrate the new concept, an actual deviation of hundreds of μm or more is common.

Figure 1D:
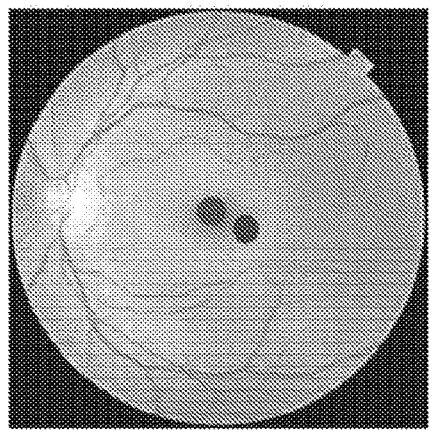
FIG. 1D shows an exemplary image of a retina camera before adjusting the translatable pinhole to find the visual axis.

FIG. 1D shows an exemplary image of a retina camera 130 before adjusting the translatable pinhole to find the visual axis. Because the translatable pinhole 120 is not yet at the visual axis, there is a non-zero transverse chromatic aberration along the current axis and correspondingly two different dots because the red light undergoes different refraction than the blue light due to transverse chromatic aberration for light entering the eye off the visual axis.

Figure 1E:
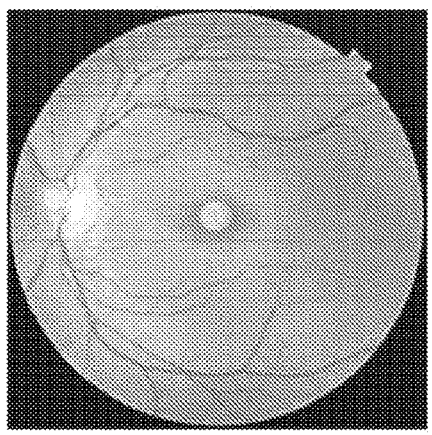
FIG. 1E shows an exemplary image of a retina camera after adjusting the translatable pinhole.

FIG. 1E shows an exemplary image of a retina camera 130 after adjusting the translatable pinhole to find the visual axis. After adjusting the translatable pinhole 120 to find the visual axis, the red spot and the blue spot have merged into one about white spot indicating substantially no transverse chromatic aberration along the now measured true visual axis.

Figure 2:
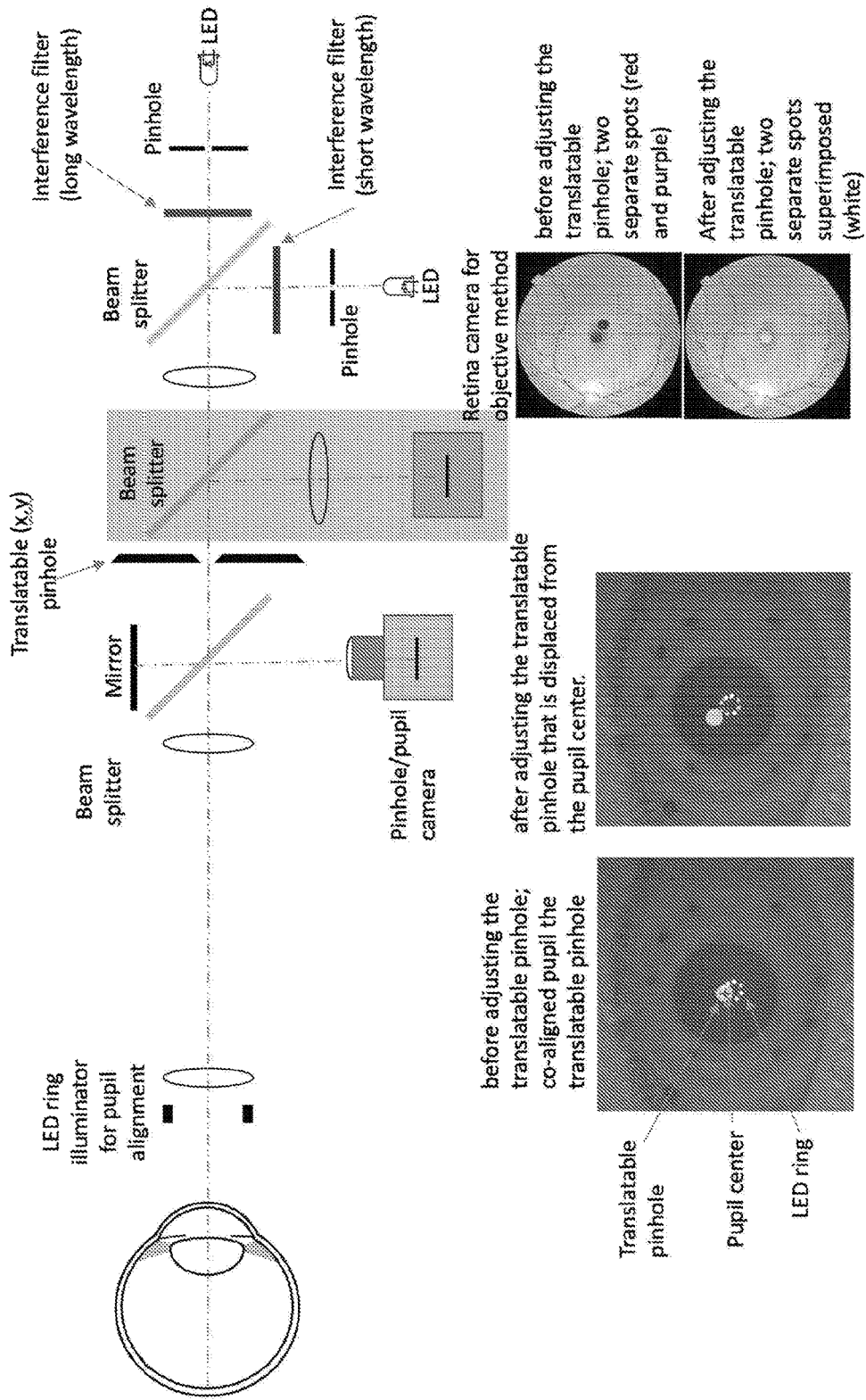
FIG. 2 shows a schematic diagram of an apparatus according to the Application where there is a pinhole in front of each of the LEDs.

FIG. 2 shows a schematic diagram of an apparatus of the same type and operation of FIG. 1A where there is a pinhole in front of each of the LEDs. As before, an image of two wavelengths is created on the surface of the retina.

Figure 3:
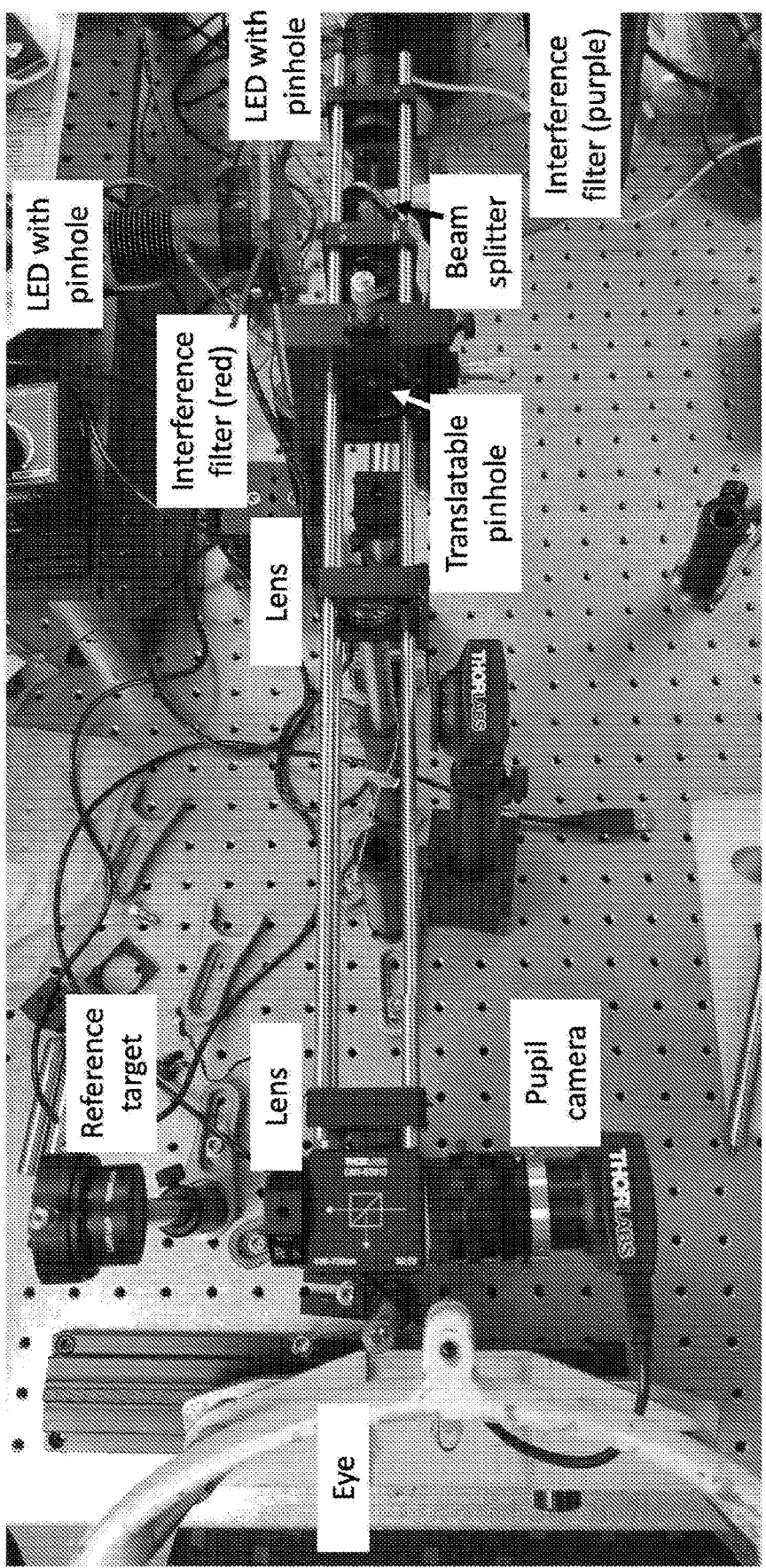
FIG. 3 is a drawing showing a laboratory proof of principle of an exemplary implementation of the new apparatus of FIG. 2.

FIG. 3 is a drawing showing a laboratory proof of principle of an exemplary non-limiting implementation of the new apparatus of FIG. 2. There is believed to be a slight advantage to the apparatus of FIG. 1A over FIG. 2, because it may be simpler to manufacture an apparatus with only the one LS pinhole 110, as opposed to aligning two different pinholes for each light source (FIG. 2) at the time of manufacture of the apparatus. The following exemplary components used in the proof of principle implementation are available from THORLABS of Newton, NJ: Interference filter part no. FB430-10/FL670-10; Translatable pinhole part no. P150D; Beam splitter part no. BP108/BS043; Pupil camera, part no. DCC1545M; Achromatic doublets, part no. AC254-100-A; and LEDs, M430L4/M660L4.

General Considerations

Light sources—It is only important that a LS pinhole image having two wavelengths be provided. Use of two different LEDs and interference filters is but one way to provide a suitable LS pinhole image. There could also be, for example, two colored LEDs (e.g. narrowband LEDs) without an interference filter. Or, there can be two different wavelength laser lights combined at a LS pinhole. Incandescent lights can also be used, typically in conjunction with interference filters. Any suitable light sources can be used. Particularly in the case where LEDs are used, the current of one or both LEDs can be made adjustable to adjust the light intensity of either or both LEDs, such as, for example, to balance the visual intensity of both color dot as observed by the patient (e.g. to compensate for a different sensitivity of the eye to different wavelengths), or as viewed by a camera, such as the retina camera.

Wavelengths—Any suitable two (or more) wavelengths can be used. Red and blue are useful because of the maximal separation in wavelength which gives a corresponding increased distance off visual axis because of the different in refraction of the two wavelengths off visual axis due to the non-zero transverse chromatic aberration. However, any suitable two wavelengths can be used. For example, the two wavelengths can typically be between about 150 nm to 300 nm apart. The interference filters should have an individual bandwidth at least about 150 nm or less in this case. However, the apparatus can function correctly with any wavelength difference which creates two spots at a discernable distance from each other. The optics, typically the front-end optical assembly, can also include magnification as desired to allow viewing (subjective and/or objective) of spots relatively close to each other. There can be manually selected, or automatically selected, two or more magnification settings, so there can be, for example, a course adjustment (lower magnification), followed by a fine adjustment (higher magnification). In the subjective mode, the spots (but, not necessarily the colors of the spots) are visible to the patient. However, in an objective mode, any wavelength spot visible to the retina camera can be used, where, for example, the longer wavelength spot can be at an IR wavelength not visible to the patient. Any suitable wavelengths can be used from IR to UV.

Pinholes—There is no significance to the different symbols used in the exemplary schematic diagrams for the translatable pinhole (shown with a bevel) and the LS pinhole. Any suitable pinhole structure or pin hole device can be used for either of the pin holes. The resolution of the location of the visual axis can be improved by reducing the size of both of the pinholes. On the smaller size, e.g. less than 5 nm, visual or image location of the spot can become difficult. In the cases of the smallest pinhole magnification can be used to assist in seeing or locating the pin hole images in either the retina or the pupil images. Of lesser importance, the intensity of the light sources can be set or adjusted as appropriate for a given pin hole size. The pinholes (LS pinhole and translatable pinhole) can be of any suitable size diameter typically from about 0.1 mm to 3 mm.

The translatable pinhole can be either manually controlled, actuator controlled, or both. A manually translated pinhole (e.g. for the subjective mode of operation) can be controlled by two micrometer manual adjustments, or any other suitable manually controlled adjustment type. Typically, such manual adjustments include gears, worm gears, micrometer controls, etc. and combinations thereof. Typically, when controlled by a processor-based process control system, the translatable pinhole is motorized with two motors, such as stepper motors. However, any suitable actuator-controlled device can be used to translate the moveable pinhole. There may, for example, be other suitable types of linear actuators that can be used, or even non-linear actuators that can move the translatable pinhole under processor control in a deterministic manner. While stepper motors are most common, the exact device used to move the translatable pinhole is unimportant.

Beam splitters—Any suitable beam splitter can be used for any of the beam splitters. The beam splitter for the LS pinhole of FIG. 1A can be a 50% beamsplitter. Or, the LS beamsplitter ratio can be selected to compensate for either different light source intensities, or more likely for different retinal sensitivity to different wavelengths of light, so that, for example, in the subjective mode, the patient sees the two different colored dots at about the same intensity.

Software and/or firmware for an apparatus described hereinabove, including firmware for a processor can be provided on a computer readable non-transitory storage medium. A computer readable non-transitory storage medium as non-transitory data storage includes any data stored on any suitable media in a non-fleeting manner Such data storage includes any suitable computer readable non-transitory storage medium, including, but not limited to hard drives, non-volatile RAM, SSD devices, CDs, DVDs, etc.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method to find a visual axis of an eye comprising:
   illuminating a light source pinhole by a light comprising at least two different wavelengths;
   projecting an image of the light source pinhole through a translatable pinhole and through a pupil of the eye onto a retina of the eye;
   generating a projected image of said translatable pinhole on an anterior surface of the eye or a contact lens;
   adjusting a position of the translatable pinhole in a plane about parallel to a plane of a cornea of the eye until two different dots viewed on the retina merge into one dot; and
   indicating by said projected image of said translatable pinhole a location of where the visual axis of the eye intersects the cornea or the contact lens.

2. The method of claim 1, wherein said step of illuminating comprises illuminating said light source pinhole by a first light source of a first wavelength and a second light source of a second wavelength.

3. The method of claim 2, wherein said step of illuminating comprises illuminating said light source pinhole by a first LED with a red interference filter or a first narrowband red LED, and a second LED with a blue interference filter or a second narrowband blue LED.

4. The method of claim 2, wherein a light of said first light source and a light of said second light source are combined by a beam splitter.

5. The method of claim 1, wherein said step of projecting comprises projecting an image of said translatable pinhole with a manual x-y position adjustment adjustable in said step of adjusting by a patient in a subject measurement mode.

6. The method of claim 1, wherein said step of projecting comprises projecting an image of said translatable pinhole with a motorized x-y position adjustment adjustable in said step of adjusting by a processor-based process in an automatic objective measurement mode.

7. The method of claim 6, wherein said step of adjusting step comprises viewing one or two dots with a retina camera.

8. The method of claim 1, wherein said step of indicating comprises viewing said projected image of said translatable pinhole on the cornea with a pupil camera.

9. An apparatus to measure a visual axis of an eye comprising:
   a light source pinhole illuminated by a first light source having at least first wavelength of light and a second light source having a second wavelength of light different from said first wavelength of light, said light source pinhole disposed on a main optical axis;
   an optical assembly about aligned with said main optical axis; and
   a translatable pinhole disposed between said optical assembly and said light source pinhole, said translatable pinhole adjustable in a plane about perpendicular to said main optical axis.

10. The apparatus of claim 9, wherein said first light source and said second light source each comprise a LED and an interference filter.

11. The apparatus of claim 9, wherein said first light source and said second light source each comprise a laser.

12. The apparatus of claim 9, wherein said first light source comprises about a red light and said second light source comprises about a blue light.

13. The apparatus of claim 9, wherein said first light source and said second light source are combined by a beamsplitter.

14. The apparatus of claim 9, wherein a lens is disposed on said main optical axis between said light source pinhole and said translatable pinhole.

15. The apparatus of claim 9, wherein said optical assembly comprises a lens or a 4f lens system.

16. The apparatus of claim 9, wherein said optical assembly further comprises a Badal optometer or a trombone system.

17. The apparatus of claim 9, further comprising a pupil camera beam splitter disposed in said main optical axis between said translatable pinhole and said optical assembly and a pupil camera disposed in a pupil camera viewing axis about perpendicular to said main optical axis and in view of said pupil camera beam splitter.

18. The apparatus of claim 9, further comprising a retina camera beam splitter disposed in said main optical axis between said light source pinhole and said translatable pinhole and a retina camera disposed in a retina camera viewing axis about perpendicular to said main optical axis and in view of said retina camera beam splitter.

19. The apparatus of claim 9, wherein said translatable pinhole comprises a two-axis motorized translatable pinhole.

20. The apparatus of claim 19, further comprising a processor operatively coupled to said two axis motorized translatable pinhole and a retina camera, said processor programmed to run a visual axis location process.

21. The apparatus of claim 20, wherein said visual axis location process automatically moves said translatable pinhole to find a position of the translatable pinhole where there is substantially no transverse chromatic aberration of a single dot image of said light source pinhole on a retina of the eye thus indicating said visual axis of the eye by an image of said translatable pinhole projected onto a cornea of the eye or a contact lens where the visual axis intersects the cornea or the contact lens.

* * * * *